(12) United States Patent
George et al.

(10) Patent No.: US 6,808,801 B2
(45) Date of Patent: Oct. 26, 2004

(54) ABSORBENT ARTICLE WITH SELF-FORMING ABSORBENT BINDER LAYER

(75) Inventors: Russell Paul George, Appleton, WI (US); Dave Allen Soerens, Neenah, WI (US); Jason Matthew Laumer, Appleton, WI (US); Cathleen Mae Uttecht, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/427,808

(22) Filed: May 1, 2003

(65) Prior Publication Data

US 2004/0018366 A1 Jan. 29, 2004

Related U.S. Application Data

(63) Continuation-in-part of application No. 10/206,883, filed on Jul. 26, 2002, now Pat. No. 6,737,491, and a continuation-in-part of application No. 10/324,478, filed on Dec. 20, 2002.

(51) Int. Cl.$^7$ ................................................ B32B 7/12
(52) U.S. Cl. ................. 428/317.7; 428/131; 428/314.2; 428/317.1; 428/913; 442/118; 442/119; 442/154; 442/155; 442/156
(58) Field of Search ............................. 428/131, 314.2, 428/317.1, 317.7, 913; 442/118, 119, 154–155, 156

(56) References Cited

U.S. PATENT DOCUMENTS

| | | | |
|---|---|---|---|
| 3,617,362 A | 11/1971 | Bemmels et al. | |
| 3,951,893 A | * 4/1976 | Gander ........................ 524/322 |
| 3,963,605 A | 6/1976 | Seabourn | |
| 4,251,643 A | 2/1981 | Harada et al. | |
| 4,291,136 A | 9/1981 | Keogh | |
| 4,328,323 A | 5/1982 | Keogh | |
| 4,343,917 A | 8/1982 | Keogh | |
| 4,353,997 A | 10/1982 | Keogh | |
| 4,369,289 A | 1/1983 | Keogh | |
| 4,408,011 A | 10/1983 | Barnabeo | |
| 4,434,272 A | 2/1984 | Keogh | |
| 4,440,907 A | 4/1984 | Keogh | |
| 4,446,279 A | 5/1984 | Keogh | |
| 4,459,396 A | 7/1984 | Yamasaki et al. | |
| 4,489,029 A | 12/1984 | Keogh et al. | |
| 4,493,924 A | 1/1985 | Rifi | |
| 4,526,930 A | 7/1985 | Keogh | |
| 4,551,504 A | 11/1985 | Barnabeo | |
| 4,575,535 A | 3/1986 | Keogh | |
| 4,579,913 A | 4/1986 | Keogh | |
| 4,593,071 A | 6/1986 | Keogh | |
| 4,676,820 A | 6/1987 | Le Sergent et al. | |
| 4,753,993 A | 6/1988 | Keogh | |
| 4,767,820 A | 8/1988 | Keogh | |
| 4,921,136 A | 5/1990 | Roggenburg, Jr. | |
| 4,940,646 A | 7/1990 | Pawlowski | |
| 5,047,476 A | 9/1991 | Keogh | |
| 5,089,564 A | 2/1992 | Bullen | |
| 5,112,919 A | 5/1992 | Furrer et al. | |
| 5,145,906 A | 9/1992 | Chambers et al. | |
| 5,196,470 A | 3/1993 | Anderson et al. | |
| 5,204,404 A | 4/1993 | Werner, Jr. et al. | |
| 5,364,382 A | 11/1994 | Latimer et al. | |
| 5,389,728 A | 2/1995 | Prejean | |
| 5,532,350 A | 7/1996 | Cottrell et al. | |
| 5,656,132 A | 8/1997 | Farrington, Jr. et al. | |
| 5,853,867 A | * 12/1998 | Harada et al. ........... 428/317.9 |
| 5,859,074 A | 1/1999 | Rezai et al. | |
| 5,911,937 A | 6/1999 | Hekal | |
| 5,932,668 A | 8/1999 | Friebe et al. | |
| 5,961,763 A | 10/1999 | Makoui et al. | |
| 6,020,071 A | 2/2000 | Watson | |
| 6,054,523 A | 4/2000 | Braun et al. | |
| 6,110,533 A | 8/2000 | Côte et al. | |
| 6,300,275 B1 | * 10/2001 | Weir .......................... 502/402 |
| 6,380,298 B2 | 4/2002 | Flautt et al. | |
| 6,403,857 B1 | 6/2002 | Gross et al. | |
| 6,417,425 B1 | 7/2002 | Whitmore et al. | |
| 6,596,402 B2 | 7/2003 | Soerens et al. | |
| 6,689,934 B2 | * 2/2004 | Dodge et al. ............... 604/367 |
| 2002/0090453 A1 | 7/2002 | Muthiah et al. | |
| 2003/0149413 A1 | 8/2003 | Mehawej | |

FOREIGN PATENT DOCUMENTS

| | | |
|---|---|---|
| CA | 756190 | 4/1967 |
| EP | 0 132 910 A2 | 2/1985 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 199 059 | 4/2002 |
| WO | 99/57201 | 11/1999 |
| WO | WO 02/053664 A2 | 7/2002 |

* cited by examiner

Primary Examiner—Helen L. Pezzuto
(74) Attorney, Agent, or Firm—Pauley Petersen & Erickson

(57) ABSTRACT

An absorbent article for personal care use includes a fluid intake layer, a flexible absorbent binder layer and a support layer. The flexible absorbent binder layer is formed between the intake layer and the support layer, and is bound to both layers. The flexible absorbent binder layer is formed from an absorbent binder composition which is applied in a liquid form, and which is capable of spontaneous crosslinking at about 120° C. or less. The absorbent article has a simplified structure and a simplified manufacturing method compared to conventional personal care absorbent articles.

18 Claims, 4 Drawing Sheets

ABSORBENT ARTICLE WITH SELF-FORMING ABSORBENT BINDER LAYER

RELATED APPLICATIONS

This application is a continuation-in-part of U.S. patent application Ser. No. 10/206,883, filed on 26 July 2002, U.S. Pat. No. 6,737,491 the disclosure of which is incorporated by reference. This application is also a continuation-in-part of U.S. patent application Ser. No. 10/324,478, filed 20 Dec. 2002, pending the disclosure of which is incorporated by reference.

BACKGROUND OF THE INVENTION

This invention is directed to an absorbent structure including a fluid intake layer, a support layer, and a self-forming absorbent binder layer holding the fluid intake layer and the support layer together.

Adhesives, or binders, are a necessary element of many absorbent products. While adhesives beneficially hold products together, adhesives may also have a tendency to interfere with the absorbency of fluids in absorbent products. Adhesives are typically hydrophobic and therefore are not conducive to absorbency or liquid transfer functions. Furthermore, most adhesives are non-absorbent and thus serve no liquid retention function.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink the water-soluble polymers. As a result of crosslinking, the material becomes swellable, and no longer soluble, in aqueous fluid. However, crosslinked polymers are difficult to apply to substrates or to establish intimate contact with surfaces because the crosslinked polymers are solid materials and have little or no ability to flow. Some of the crosslinked materials are fairly stiff, and inhibit the flexibility of the absorbent product.

What is therefore needed is a hydrophilic binder or coating that has latent crosslinking capability and which can be produced at attractive cost. Such binder or coating could be easily applied, like a water-soluble polymer, since the hydrophilic binder or coating would be capable of flow prior to crosslinking. Latent crosslinking capability would also provide a simple means of crosslinking the polymer after the polymer has established intimate contact with substrates or has formed a desired final shape or form. There is also a need or desire for such a binder which has a high level of flexibility.

Post-application crosslinking techniques are well known. Typical means of inducing the formation of crosslinks include high temperature "curing" or exposure to radiation, such as ultraviolet or gamma radiation. Another known means of post-application crosslinking is moisture-induced crosslinking.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processable, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

These examples of moisture-induced crosslinking are applied to substantially hydrophobic polymers. Since the cured products of these formulations are reported to be useful for coverings for wire and cable, and for non-conductive coatings for electrical conductors, and for painting and refinishing the exterior of automobiles, it would be expected that they are durable coatings for which properties such as water absorbency would be a disadvantage.

Conventional personal care absorbent articles including diapers, training pants, sanitary napkins, adult incontinence garments and the like, have a relatively complex structure and manufacturing procedure. Personal care absorbent articles typically include a liquid-permeable bodyside liner, a surge (compensation) layer which receives and distributes liquid received through the liner, a single-layer or multiple-layer absorbent core which receives and stores liquid that passes through the compensation layer, and a liquid-impermeable outer cover that prevents liquid in the absorbent article and provides a substantially dry outer surface. Each of these layers is separately manufactured. The layers are then combined using adhesive bonding, thermal bonding, ultrasonic bonding and other techniques which must be tailored to sufficiently bond the layers together without compromising their respective functions. There is a need or desire for absorbent articles having simpler structures that can be manufactured using simpler, less expensive techniques.

SUMMARY OF THE INVENTION

This invention is directed to a three-layer absorbent structure and to absorbent articles containing it. The three-layer absorbent structure includes the following layers, in sequence, with no additional adhesive or other layers in between them:

a) a liquid-permeable fluid intake layer, b) a flexible absorbent binder layer, and c) a support layer.

The flexible absorbent binder layer serves as a fluid storage (absorbent) layer and also bonds the fluid intake layer to the support layer. The absorbent article may contain additional layers, so long as the above three layers of the absorbent structure occur in sequence. In some absorbent articles, the three-layer absorbent structure may not be accompanied by additional layers.

The three-layer absorbent structure is formed by applying an absorbent binder composition to one or both facing surfaces of the fluid intake layer and the support layer, bringing the fluid intake layer and support layer together, and crosslinking the absorbent binder composition to form the flexible absorbent binder layer. Because the flexible absorbent binder layer is formed (crosslinked) while the absorbent binder composition is in contact with the other layers, the flexible absorbent binder layer serves both as an absorbent layer and an adhesive (binder) layer in the three-layer absorbent structure, eliminating the need for additional adhesive or other bonding steps.

The absorbent binder composition includes about 15 to about 99.9% by mass of monoethylenically unsaturated polymer units. Suitable monoethylenically unsaturated polymers include without limitation carboxylic acid, sulphonic acid, phosphonic acid, and salts of the foregoing. The absorbent binder composition also includes about 0.1 to about 20% by mass of acrylate or methacrylate ester units that include an alkoxysilane functionality. Upon exposure to water, the alkoxysilane functionality forms a silanol group which condenses to form a crosslinked polymer.

The absorbent binder composition may also include zero to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the absorbent binder composition with enhanced flexibility. Thus, the flexible absorbent binder layer has enhanced adhesion in a wet condition, absorbency, and flexibility.

The absorbent binder composition may be used to form a flexible absorbent binder layer on and between such layers as nonwoven webs, woven webs, foams, knitted fabrics, cellulose tissue, plastic film, stranded composites, staple fibers, yarns, elastomer net composites, or any other suitable substrates. Examples of plastic film substrates include those made of polypropylene, low density polyethylene, high density polyethylene, linear low density polyethylene, and ultra low density polyethylene. Examples of absorbent articles in which the three-layer absorbent structure may be used include diapers, diaper pants, training pants, feminine hygiene articles, swim wear, adult incontinence garments, swimwear garments, medical absorbent articles, and the like.

The absorbent binder composition can be prepared using a template polymerization process by which the monoethylenically unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting absorbent binder composition may contain the polyolefin glycol and/or oxide as a separate component, or as part of the copolymer, or a combination of both.

The resulting absorbent binder composition has latent moisture-induced crosslinking capability due to the alkoxysilane functionality. The composition may be applied, in a flowable state, to the fluid intake layer and/or support layer. After the layers are brought together, moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

With the foregoing in mind, it is a feature and advantage of the invention to provide a three-layer, absorbent structure having a self-forming absorbent binder layer, and absorbent articles including the three-layer absorbent structure.

Definitions

Within the context of this specification, each term or phrase below will include the following meaning or meanings.

"Binder" includes materials which are capable of attaching themselves to a substrate or are capable of attaching other substances to a substrate.

"Feminine hygiene products" include sanitary pads and napkins, as well as tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 g/cm³ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to about 0.935 g/cm³.

"Low density polyethylene (LDPE)" refers to a polyethylene having a density between about 0.91 and about 0.925 g/cm³.

"Modifying agent" refers to a substance that may be added to a composition to modify the physical properties of the composition, such as the color or texture of the composition.

"Nonwoven" or "nonwoven web" refers to materials and webs or material having a structure of fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care absorbent product" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, or a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 10 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. A material is "absorbent" if it absorbs at least five times its weight of the aqueous solution under these conditions.

"Unit" or "polymer unit" refers to a monomer or polymer portion of a copolymer molecule or blend component that includes a different molecular structure, compared to another portion of the copolymer or blend.

DETAILED DESCRIPTION OF THE PRESENTLY PREFERRED EMBODIMENTS

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 1:
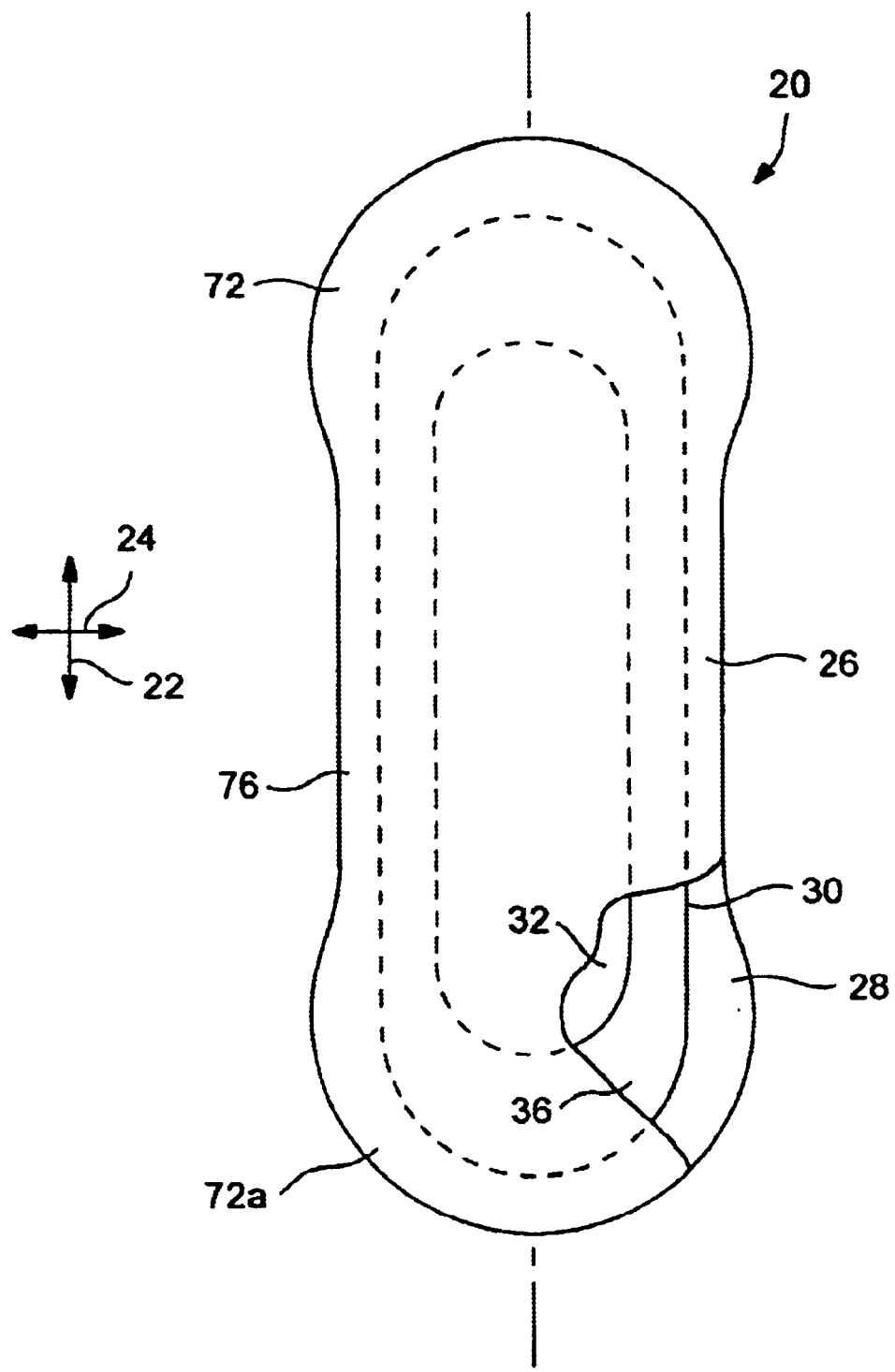
FIG. 1 is a top view of a conventional absorbent article, in this case a sanitary napkin, partially cut away to expose the underlying layers.
Figure 1A:
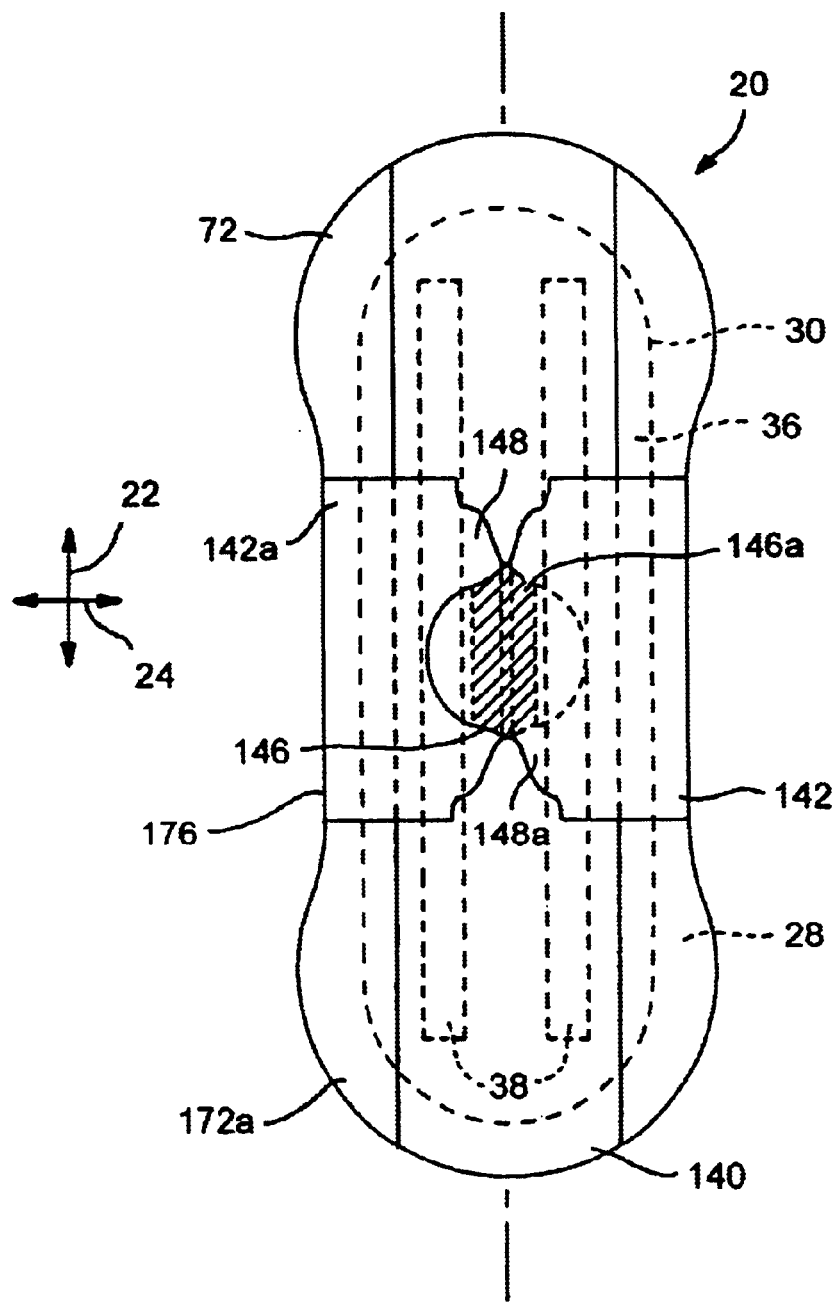
FIG. 1A is a partially cut away bottom view of the absorbent article of FIG. 1.
Figure 1B:
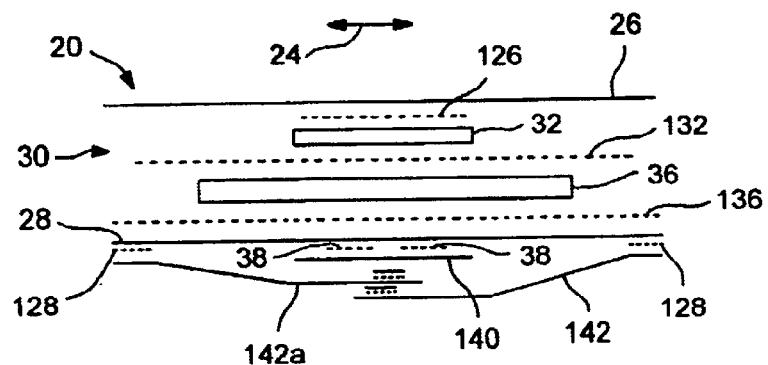
FIG. 1B is a sectional view of the absorbent article of FIG. 1, taken along a lateral direction 24 through the longitudinal center of the article.
Figure 1C:
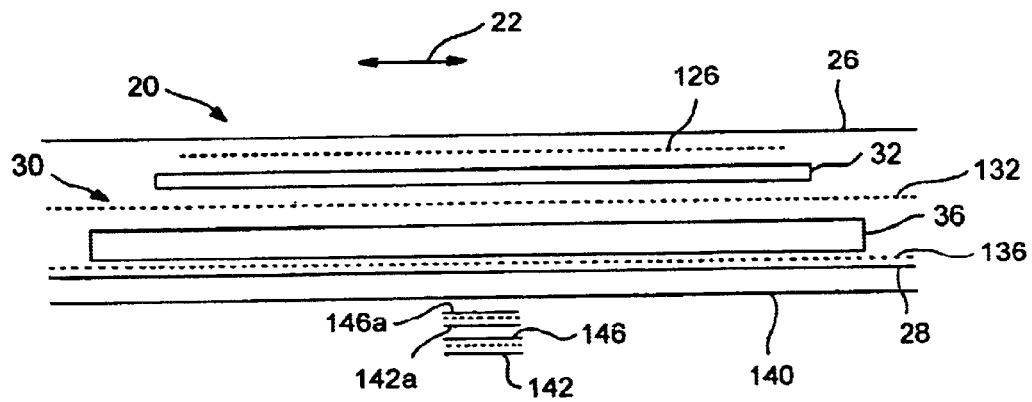
FIG. 1C is a sectional view of the absorbent article of FIG. 1, taken along a longitudinal direction 22 through the lateral center of the article.

FIGS. 1 through 1C illustrate an example of a suitable article, such as the representatively shown feminine care article. Referring to FIG. 1, the feminine care article can, for example, be a feminine care pad or napkin 20, and the article can have a lengthwise longitudinal direction 22, a transverse, laterally extending cross-direction 24, first and second longitudinally opposed end portions 172 and 172a, and an intermediate portion 176 located between the end portions. As representatively shown, the longitudinal dimension of the article is relatively larger than the lateral dimension of the article. The article 20 can include a topsheet or cover 26, a baffle 28, and an absorbent structure 30 positioned between the cover and baffle. The absorbent structure 30 can at least include an intake layer 32 and a shaping or absorbent layer 36.

Referring to FIG. 1, the absorbent article 20, in this case a sanitary napkin, may embody or be replaced by an absorbent structure of the invention. In the lower section of FIG. 1 layers, respectively, of the article 20 of the invention have in part been cut out to show the layers below. The lowermost layer (outer cover or baffle) of the article 20 is formed by a liquid-impermeable layer 28. The liquid-impermeable layer 28 can be made of a polypropylene film, for instance. The liquid-impermeable layer 28 serves as so-called garment-protecting layer which prevents liquid which has penetrated into the absorbent article and which is retained therein from escaping downwards from the absorbent body. This prevents the wearer's undergarment from being stained. The liquid-impermeable layer 28, which is referred to synonymously as an outer cover or baffle, can be breathable to water vapor.

Referring to FIG. 1A, the absorbent article 20 also includes two laterally extending, inward folding wings 142 and 142a, hook fastening materials 146 and 146a attached to inner surfaces of end regions of the wings, respectively, and loop fastening materials 148 and 148a attached to or forming part of outer surfaces of the user's end regions of the wings. When the wings 142 and 142a are folded inward as shown, over a wearer's garment, the hook and loop fastening regions overlap and engage each other to secure the absorbent article 20 in place. Adhesive bands 38 can be used to secure the baffle 28 to a peelable release layer 140. When the release layer 140 is removed (peeled away), the bands 38 of adhesive provide additional securement of the absorbent article 20 to an inner surface of the wearer's garment.

FIGS. 1B and 1C illustrate exploded sectional views of the absorbent article 20, shown in the lateral direction 124 (FIG. 1B) and in the longitudinal direction 122 (FIG. 1C). As illustrated, the topsheet 26 and intake layer 32 are adhered together by a first adhesive layer 126. The intake layer 32 and absorbent layer 36 are adhered together by a second adhesive layer 132. The absorbent layer 36 and baffle 28 are adhered together by a third adhesive layer 136. The wings 142 and 142a may be bound at manufacturer's ends thereof to the baffle 28 by adhesive bands 128.

Additional absorbent structures, namely feminine care pad designs, are described in U.S. patent application Ser. No. 10/379,942, filed on 04 Mar. 2003, entitled "Perimeter Embossing In An Absorbent Article," and in U.S. patent application Ser. No. 10/392,116, filed on Mar. 19, 2003, entitled "Multilayer Absorbent Article." These documents are incorporated by reference.

As described above, the absorbent article of FIGS. 1–1C includes multiple fluid receiving layers (topsheet 26, fluid intake layer 32) an absorbent layer 36, an outer cover or baffle 28, and multiple adhesive layers (126, 132 and 136) holding these layers together.

Figure 2:
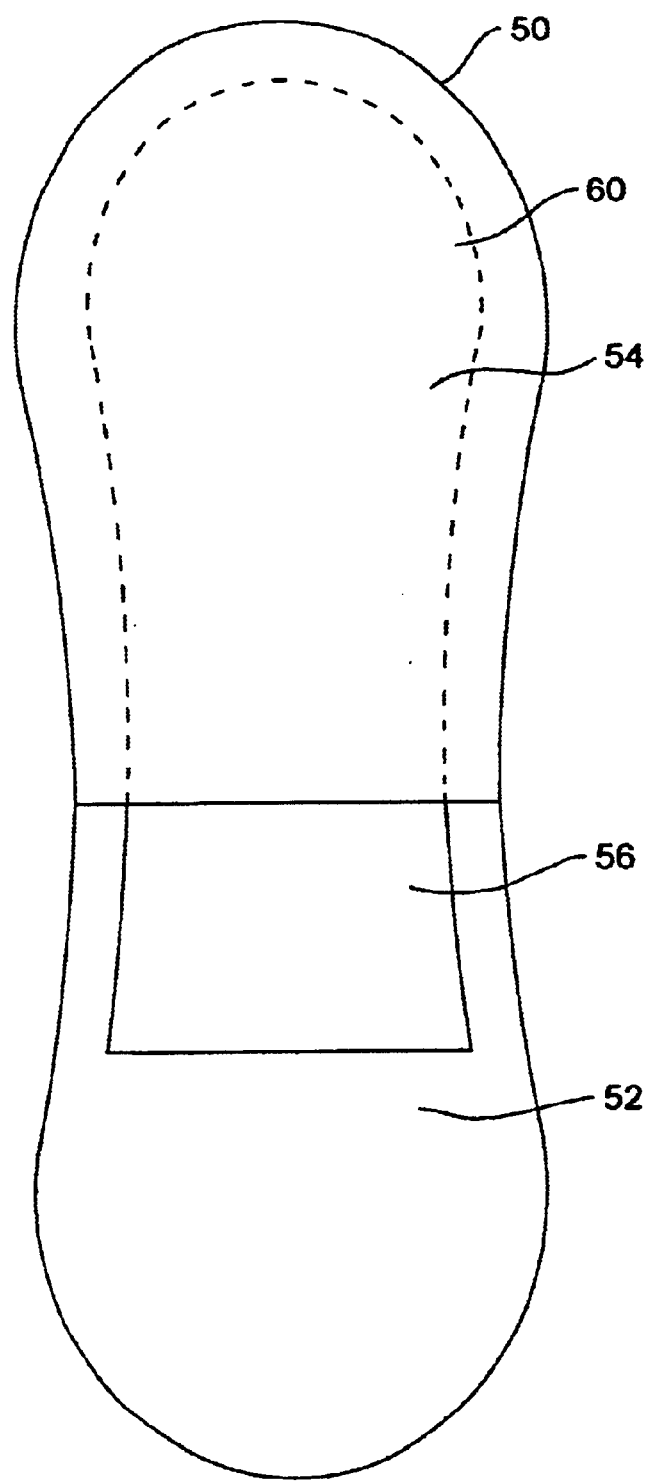
FIG. 2 is a plan view of an absorbent article of the invention having a simplified three-layer structure, partially cut away to expose the underlying layers.

FIG. 2 illustrates an absorbent article 50 formed using the simplified three-layer absorbent structure 54 of the invention. The absorbent article 50 illustrated includes three layers, namely a liquid intake layer 60, a layer 56 of flexible absorbent binder, and a support layer 52. In the embodiment shown, the intake layer 60 is also a bodyside liner, and the support layer 52 is an outer cover. The flexible absorbent binder layer 56 is directly joined to the adjacent functional layers 52 and 60, without an additional adhesive. This is accomplished by applying an absorbent binder composition to facing surfaces of one or both layers 52 and 60, bringing the layers 52 and 60 together so that the absorbent binder composition contacts both layers, and crosslinking the absorbent binder composition to form the flexible absorbent binder layer 56. The flexible absorbent binder is an absorbent or superabsorbent polymer formed using techniques described below.

Because the flexible absorbent binder layer 56 is in contact with layers 52 and 60 as it is being formed, the layer 56 adheres to layers 52 and 60 in addition to serving as an absorbent (fluid storage) layer. Thus, the absorbent structure 54 of the invention provides three layers bound together in sequence, namely a fluid receiving layer, a flexible absorbent binder layer, and a support layer, without intervening adhesive layers.

The flexible absorbent binder layer 56 may be formed as a continuous layer having uniform thickness, or as a discontinuous or nonuniform layer which provides flow channels, liquid retention dams, or other desired attributes. However, because the flexible absorbent binder layer 56 is intended as a sole or primary absorbent layer in the simplified absorbent article, the flexible absorbent binder should be present in sufficient thickness and quantity, and over a sufficient area to provide substantially all of the liquid absorption capacity that is required by the end use application. Alternatively, superabsorbent particles can be incorporated into the flexible absorbent binder layer 56 to provide a portion of the liquid absorption capacity required by the end use application.

The absorbent article 50 may include only the three layers 52, 56 and 60 forming the absorbent structure 54, or may include additional layers on one or both sides of the absorbent structure 54 (but not between the layers 52, 56 and 60). In either case, the absorbent article 50 will have a simplified construction compared to conventional absorbent articles because a) the flexible absorbent binder layer 56 (with or without superabsorbent particles) provides essentially all of the required absorbent capacity, and b) the flexible absorbent binder layer 56 binds to the adjacent layers 52 and 60 without intervening adhesive layers.

The absorbent binder composition used to form the flexible absorbent binder layer 56 includes about 15 to about 99.9% by mass of monoethylenically unsaturated polymer units, suitably about 25 to about 90% by mass, particularly about 30–80% by mass, or about 50 to about 70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides (such as maleic anhydride);

c) Carboxylic acid salt group-containing monomers including water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

d) Sulfonic acid group-containing monomers, including aliphatic or aromatic vinyl sulfonic acids (such as vinylsulfonic acid, allyl sulfonic acid, vinyltoluene-sulfonic acid, stryrene sulfonic acid), (meth)acrylic sulfonic acids [such as sulfopropyl (meth)acrylate, 2-hydroxy-3-(meth)acryloxy propyl sulfonic acid];

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth) acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], 3-acrylamidopropyl trimethyl ammonium chloride, vinyl lactams (such as N-vinylpyrrolidone).

The absorbent binder composition also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the absorbent binder composition may include about 0.5 to about 15% by mass of the acrylate and/or methacrylate ester units, for instance about 1.0 to about 10% by mass, for instance about 1.5 to about 5.5% by mass.

The alkoxysilane functionality is a functional group or moiety that reacts with water to form a silanol group. One suitable alkoxysilane group is a trialkoxy silane group having the following structure:

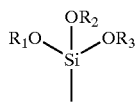

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with mono-ethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particular ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxy-ethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects and are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the copolymer may subsequently be reacted with, for example, but not limited to, tetramethoxysilane.

The absorbent binder composition may also include zero to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000.

Polyolefin glycols and polyolefin oxides are commercially available, and are common. To prepare the absorbent binder composition, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting absorbent binder composition includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. Suitable classes of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator.

Alternatively, redox initiation can be used for the polymerization. This method incorporates a first monomer solution that includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g., a redox reaction, thereby initiating a polymerization reaction to form a binder composition including a monoethylenically unsaturated monomer and an ethylenically unsaturated monomer that has post-application, moisture-induced crosslinking capability.

In one embodiment, the monoethylenically unsaturated polymer unit is a cationic polymer. The cationic polymer is advantageous because it provides a) inherent antimicrobial properties, b) enhanced attraction and retention into cellulose fibers in a suspension, and c) enhanced attraction to superabsorbent particles which are negatively charged. Suitable cationic polymers include those prepared by copolymerizing a monomer 1) selected from a) acryloyloxyethyl-trialkyl-substituted ammonium salts, b) acryloyloxypropyl-trialkyl-substituted ammonium salts, c) acrylamidoethyl-trialkyl-substituted ammonium salts, and d) acrylamidopropyl-trialkyl-substituted ammonium salts, with a monomer 2) selected from a) methacryl esters which contain an alkoxysilane group capable of moisture-induced crosslinking and b) acryl esters which contain an alkoxysilane group capable of moisture-induced crosslinking. Other monomers may also be present, for instance, an acrylic acid or acrylamide. The polymerization is conducted in the presence of a polyolefin glycol and/or polyolefin oxide as described above, suitably a polyethylene glycol. The cationic monoethylenically unsaturated monomer unit and the polyolefin glycol are present in the amounts described above.

The cationic monoethylenically unsaturated polymer may be prepared by a redox initiation process, according to the following reaction. The cationic copolymer is then coated and dried between the fluid receiving layer 60 and the support layer 52 to form the flexible absorbent binder layer 56.

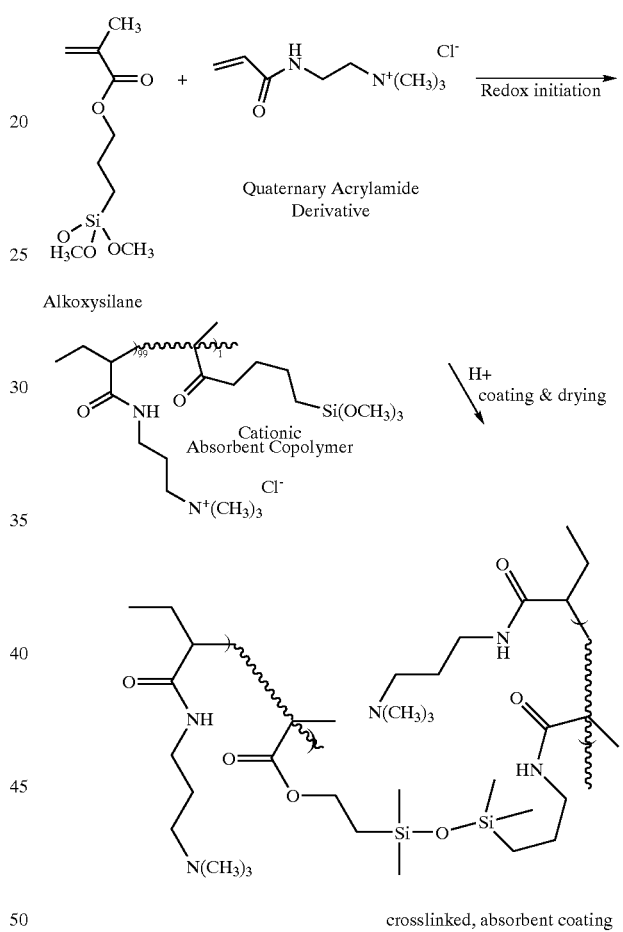

In one embodiment, the absorbent binder composition is made by combining a first aqueous monomer solution including a reducing polymerization initiator with a second aqueous monomer solution including an oxidizing polymerization initiator, wherein the initiators react to form the absorbent binder composition. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the absorbent binder composition is formed in about 100 minutes or less, or about 60 minutes or less, desirably in about 30 minutes or less, or about 15 minutes or less, or about 10 minutes or less.

The pH of the first and/or second aqueous monomer solution is adjusted to about 4.5 to about 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to about 8, suitably about 5.5 to about 7.0.

The amounts of the polymerization ingredients added to the first and second aqueous solutions are selected so as to produce the absorbent binder composition having the composition described above. In one embodiment, a surfactant may be added to the first and/or second aqueous monomer solution to disperse the ethylenically unsaturated monomer.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form the absorbent binder composition including a monoethylenically unsaturated monomer and an ethylenically unsaturated monomer that has post-application, moisture-induced crosslinking capability.

The absorbent binder composition is applied to the layers 52 and/or 60, and the layers are brought together so that the absorbent binder composition contacts each layer. The absorbent binder composition is dried. To form the flexible absorbent binder layer 56, crosslinking can be moisture-induced by hydrolysis and condensation of alkoxysilanes. For example, crosslinking of the absorbent binder composition can be induced by concentrating the binder composition through the removal of the water to promote condensation of silanols generated by hydrolysis of alkoxysilanes. Typically, crosslinking begins at a solution concentration of about 30 percent or greater by weight binder composition.

The absorbent binder composition may be applied in any concentration that provides a viscosity suitable for the application process. The absorbent binder composition may be applied to the substrate using any suitable application process, including knife over roll coating, or roll coating, either in a continuous coverage or a patterned coverage. Printing applications are other suitable application techniques, including gravure printing, screen, and jet printing. The absorbent binder composition may also be applied to the substrate using a spray application. Again, enough of the absorbent binder composition should be applied to form a flexible absorbent binder layer 56 having sufficient absorbent capacity.

In another embodiment, the absorbent binder composition may be prepared using a continuous process wherein the polymerization and/or neutralization reaction is carried out in a suitable reactor that conveys the resulting binder composition, upon completion of the polymerization reaction, directly to an apparatus for applying the absorbent binder composition onto the layer 52 and/or 60. Such a continuous process may be desirable where conditions, such as high heat, may cause premature crosslinking of the binder composition that would hinder application of the absorbent binder composition onto the substrate.

One advantage of the absorbent binder composition is that it provides a water-soluble ionic polymer capable of sufficient spontaneous crosslinking within about 10 minutes, at a temperature not more than about 120° C., to provide the flexible absorbent binder layer with an absorbent capacity of at least one gram of fluid per gram of flexible absorbent binder layer, suitably at least three grams of fluid per gram of flexible absorbent binder layer, using the centrifuge retention capacity test described herein. The term "spontaneous" crosslinking refers to crosslinking which occurs without radiation, catalysis, or any other inducement other than the specified temperature of not more than about 120° C., suitably not more than about 100° C. Eliminating the need for radiative crosslinking provides a significant processing advantage. The crosslinking at temperatures not more than about 120° C., suitably not more than about 100° C., permits the absorbent binder composition to be applied to one or more substrate layers, and then crosslinked without degrading or damaging the substrate. Significant crosslinking occurs within about 10 minutes, suitably within about 8 minutes, particularly within about 6 minutes provides an efficient, commercially feasible, cost-effective crosslinking process. The crosslinking may then continue until flexible absorbent polymer having the desired absorbent capacity is obtained. The ionic polymer may bear a positive charge, a negative charge, or a combination of both, and should have an ionic unit content of about 15 mole percent or greater. The ionic polymer may include a variety of monomer units described above, and suitably contains a carboxyl group-containing unit or a quaternary ammonium-containing unit.

Referring again to FIG. 2, the support layer 52 may be a liquid-impermeable outer cover material. Suitable outer cover materials include without limitation polyolefin films (e.g., films of polypropylene and polyethylene homopolymers and copolymers), breathable polyolefin films (e.g., stretch-thinned films formed from one or more polyolefins blended with calcium carbonate or other suitable particulate fillers), and laminates of a breathable polyolefin film and a polyolefin nonwoven web (e.g., a spunbond web). Alternatively, the absorbent article 50 may be designed to include one or more functional layers, such as a dampness-inhibiting "spacer" structure, between the outer cover and the flexible absorbent polymer layer 56. In such instances, the support layer 52 may be any layer that is positioned directly below the flexible absorbent polymer layer 52 in the absorbent article 50. Depending on the application, the support layer 52 may be a nonwoven web, woven web, knitted fabric layer, cellulose layer, plastic film, plastic foam, staple fiber layer, elastomeric net composite, stranded composite or another suitable material.

The fluid-receiving layer 60 may be an apertured film, an open nonwoven layer such as a spunbond layer, bonded carded web or staple fiber web, an open-celled (e.g., reticulated) foam, a cellulose web, or any suitable open structure capable of receiving and/or distributing liquid. The fluid-receiving layer 60 may be homogeneous in the thickness direction or have a gradient structure. The desired composition of fluid receiving layer 60 may depend on whether the fluid-receiving layer 60 is used as a bodyside liner, or whether it is an interior fluid-receiving layer (e.g., a surge/transfer or compensation layer) used in addition to one or more other fluid receiving layers. In the simplest embodiment, the absorbent article 50 may include only the three-layer absorbent structure 54 composed of the fluid receiving layer 60, flexible absorbent binder layer 56 and support layer 52. In other embodiments, the three-layer absorbent structure 54 may form only a part of a more complex layer structure in an absorbent article 50.

Test Method For Determining Absorbent Capacity

As used herein, the Centrifuge Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #1234T) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5 inch). Three sample bags are tested for each material.

The sealed bags are submerged in a pan of 0.9% NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at 1600 rpm, for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent structure comprising the following three layers in sequence and bound to each other with no additional layers between them:
   a) a fluid intake layer;
   b) a flexible absorbent binder layer; and
   c) a support layer;
   wherein the flexible absorbent binder layer is formed between and bound to the fluid intake layer and the support layer by crosslinking an absorbent binder composition including a water-soluble ionic polymer capable of sufficient non-radiative crosslinking within about 10 minutes at a temperature of about 120° C. or less, to reach an absorbent capacity of at least one gram per gram using the centrifuge retention capacity test, while the absorbent binder composition is in contact with fluid intake layer and the support layer.

2. A diaper comprising the absorbent structure of claim 1.

3. A training pant comprising the absorbent structure of claim 1.

4. A diaper pant comprising the absorbent structure of claim 1.

5. A feminine hygiene article comprising the absorbent structure of claim 1.

6. An adult incontinence garment comprising the absorbent structure of claim 1.

7. A swimwear garment comprising the absorbent structure of claim 1.

8. A medical absorbent article comprising the absorbent structure of claim 1.

9. The absorbent article of claim 1, wherein the flexible absorbent binder is formed by crosslinking an absorbent binder composition including about 15 to about 99.9% by mass of monoethylenically unsaturated polymer units, about 0.1 to about 20% by mass polyacrylate ester units selected from the group consisting of acrylate and methacrylate units that include an alkoxysilane functionality, and zero to about 75% by mass of units selected from the group consisting of polyolefin glycol and polyolefin oxide units.

10. The absorbent structure of claim 1, wherein the flexible absorbent binder layer is formed by crosslinking an absorbent binder composition including about 25 to about 20% by mass of monoethylenically unsaturated polymer units, about 0.5 to about 15% by mass polyacrylate ester units that include an alkoxysilane functionality, and about 10 to about 60% by mass polymer units, and combinations thereof.

11. The absorbent structure of claim 1, wherein the fluid intake layer comprises a bodyside liner.

12. The absorbent structure of claim 1, wherein the fluid intake layer comprises a surge/transfer layer.

13. The absorbent structure of claim 1, wherein the fluid intake layer comprises a material selected from the group consisting of apertured films, spunbond webs, staple fiber webs, open-celled foams, cellulose webs and combinations thereof.

14. The absorbent structure of claim 1, wherein the fluid intake layer comprises a reticulated foam.

15. The absorbent structure of claim 1, wherein the support layer comprises an outer cover.

16. The absorbent structure of claim 1, wherein the support layer comprises a spacer.

17. The absorbent structure of claim 1, wherein the support layer comprises a material selected from polyolefin films, breathable polyolefin films including a polyolefin blended with a particulate filter, breathable film/nonwoven web laminates, and combinations thereof.

18. An absorbent stsorbent comprising the following three layers in sequence and bound to each other:
   a) a fluid intake layer;
   b) a flexible absorbent binder layer; and
   c) a support layer;
   wherein the flexible absorbent binder layer is formed between the fluid intake layer and the support layer by crosslinking an absorbent binder composition including a water-soluble ionic polymer capable of sufficient non-radiative crosslinking within about 10 minutes at a temperature of about 120° C. or less, to reach an absorbent capacity of at least one gram per gram using the centrifuge retention capacity test, and is formed by crosslinking an absorbent binder composition including about 25 to about 90% by mass of monoethylenically unsaturated polymer units, about 0.5 to about 15% by mass polyarcrylate ester units that include an alkoxysilane funtionality, and about 10 to about 60% by mass polymer units selected from the group consisting of polyolefin glycol units, polyolefin oxide units, and combinatiions thereof.

* * * * *